United States Patent [19]

Takase

[11] Patent Number: 4,849,886

[45] Date of Patent: Jul. 18, 1989

[54] SYSTEM FOR IMPROVING THE SIN RATIO OF A NMR SIGNAL BY SUMMING IN PHASE COSINE AND/OR SINE COMPONENTS

[75] Inventor: Hidetomo Takase, Tokyo, Japan

[73] Assignee: Tokyo Shibaura Denki Kabushiki Kaisha, Kawasaki, Japan

[21] Appl. No.: 178,850

[22] Filed: Apr. 1, 1988

Related U.S. Application Data

[63] Continuation of Ser. No. 564,916, Dec. 23, 1983, abandoned.

[30] Foreign Application Priority Data

Dec. 27, 1982 [JP] Japan .................... 57-226972

[51] Int. Cl.[4] .................. G01N 24/08; A61B 5/05
[52] U.S. Cl. .................. 364/413.13; 324/309
[58] Field of Search .............. 364/413, 414, 415, 417, 364/602, 724, 825, 413.13; 378/4, 5, 21, 901; 358/111, 160, 166, 167, 903; 324/61 R, 233, 228, 307, 309, 312

[56] References Cited

U.S. PATENT DOCUMENTS

| | | | |
|---|---|---|---|
| 3,297,860 | 1/1967 | Weiss | 235/151.35 |
| 3,999,118 | 12/1976 | Hoult | 324/0.5 A |
| 4,204,225 | 5/1980 | Mistretta | 358/111 |
| 4,204,226 | 5/1980 | Mistretta et al. | 358/111 |
| 4,250,451 | 2/1981 | Slagle | 324/228 X |
| 4,297,637 | 10/1981 | Crooks et al. | 324/309 |
| 4,307,344 | 12/1981 | Walters | 324/307 |
| 4,315,216 | 2/1982 | Clow et al. | 324/309 |
| 4,430,749 | 2/1984 | Schardt | 364/414 X |
| 4,468,621 | 8/1984 | Hinshaw | 324/309 |
| 4,480,228 | 10/1984 | Bottomley | 324/309 |
| 4,493,039 | 1/1985 | Gregory | 364/414 |
| 4,599,565 | 7/1986 | Hoenninger, III et al. | 324/309 |
| 4,602,214 | 7/1986 | Edelstein et al. | 324/309 |

FOREIGN PATENT DOCUMENTS

2113850A 1/1982 United Kingdom .

OTHER PUBLICATIONS

Lindon et al., "Digitisation and Data Processing in Fourier Transform NMR," Progress in NMR Spectroscopy, vol. 14, pp. 27-43, 1980.

Mono et al., "Microcomputer Based Phase Sensitive Detector," Journal of Physics E. Scientific Instruments, vol. 14, No. 11, Nov. 1981, pp. 1253-1256.

*Primary Examiner*—Clark A. Jablon
*Attorney, Agent, or Firm*—Finnegan, Henderson, Farabow, Garrett & Dunner

[57] ABSTRACT

In a nuclear magnetic resonance (NMR) diagnostic apparatus, the NMR signals from a portion of an object excited repeatedly by the same type excitation pulses are temporarily stored and the signal-to-noise (S/N) ratio thereof is improved by summing together at least two cos signal components, or two sin signal components of the NMR signals which were taken during these examination periods. An image processing circuit is used to process the NMR signals with impioned S/N ratio so as to obtain a tomographic image of the object.

16 Claims, 6 Drawing Sheets

$\Delta E = \gamma \hbar H_0$

SYSTEM FOR IMPROVING THE SIN RATIO OF A NMR SIGNAL BY SUMMING IN PHASE COSINE AND/OR SINE COMPONENTS

This application is a continuation of application Ser. No. 06/564,916, filed Dec. 23, 1983 abandoned.

BACKGROUND OF THE INVENTION

This invention relates to a nuclear magnetic resonance diagnostic apparatus which utilizes the nuclear magnetic resonance phenomenon (referred to as "NMR" phenomenon hereinafter) so as to noninvasively measure information concerning the spin density and relaxation time of a specific atomic nucleus or a proton within a selected sectional slice plane of an object to be examined, e.g., a patient, for which a tomographic image is obtained with a high S/N ratio.

First, the principle of an NMR apparatus will be summarized.

Atomic nuclei are composed of protons and neutrons. It is generally considered that they are spinning as a whole like a top. In other words, an atomic nucleus of hydrogen ($^1$H) is comprised of one proton which is spinning in a manner indicated by spin quantum number $\frac{1}{2}$ as shown in FIG. 1A. Also shown in FIG. 1B, since the proton holds a positive charge (e+), rotating nuclei of hydrogen may be considered equivalent to a current corresponding to the above positive charge flowing in a small coil. As a result, a magnetic moment $\vec{\mu}$ occurs. In other words, a respective nucleus of hydrogen can be regarded as a very small magnet. In general, as schematically shown in FIG. 2A in ferromagnetic materials such as an iron, all of the very small magnets are oriented in the same direction, so that a macroscopic magnetization '37 M" can be observed. To the contrary, since each of the magnetic moments in the nucleus of hydrogen is oriented at random, the macroscopic magnetization cannot be observed as shown in FIG. 2B. If a static magnetic fields $H_O$ is applied to the nuclei, each of the nuclei is directed toward a magnetization direction of the field $H_O$ (,i.e., an energy level of the nucleus is quantized in the Z direction). This condition of the nuclei of hydrogen is displayed in FIG. 3A. As the nucleus of hydrogen has $\frac{1}{2}$ quantum number, the nuclei of hydrogen are divided into two energy levels, i.e., $-\frac{1}{2}$ and $+\frac{1}{2}$. Most of the divided hydrogen nuclei are oriented in the Z direction corresponding to $+\frac{1}{2}$ energy level.

A difference between these two energy levels is given by formular (1);

$$\Delta E = \gamma H_O \tag{1}$$

where $\gamma$ is a gyromagnetic ratio (the ratio between the magnet and mechanical moments), $\hbar$ is a Plank's constant and is equal to $h/2\pi$.

Since the static magnetic field $\vec{H}_O$ is being applied to each of the hydrogen nuclei so that a force indicated by $\vec{\mu} \times \vec{H}_O$ is applied thereto, each of the hydrogen nuclei rotates around the Z axis at an angular velocity of $\omega = \gamma H_O$ (i.e. the Larmor angular velocity). Under these conditions of the nuclei of hydrogen when an electromagnetic wave (normally a radiofrequency wave) having a frequency corresponding to the angular velocity $\omega$ is applied, a nuclear magnetic resonance occurs. As a result, the nuclei of hydrogen absorb an energy $\gamma \cdot H_O$ which corresponds to the above-mentioned energy level difference ($\Delta E$), so that transition of the nuclei of hydrogen occurs to a higher energy level. Although there exist several kinds of nuclei in one object which have their own respective spin angular momentum, it is possible to pick up a resonance of a specific atomic nucleus only, because each of the nuclei has its specific gyromagnetic ratio $\gamma$, and each of them has different resonance frequency. Moreover if an amplitude of the resonant signal is measured, the density of the atomic nucleus in the object can be obtained. The nucleus which has been excited to the high energy level returns to the lower energy level after the occurence of the nuclear magnetic resonance in a period of time that is defined by a time constant (i.e. the so-called "relaxation time"). The relaxation time includes a spin-lattice relaxation time "T1" and a spin-spin relaxation time "T2". The spin-lattice relaxation time "T1" and the spin-spin relaxation time "T2' are such time constants that they are decided depending upon the combination of the composition of the object. For example, values of those relaxation times for the normal tissue are different from that for the malignant tumor.

Although the above description will cover only hydrogen-1, it is obvious that similar measurements can be applied to other atomic nuclei having spin angular momentums different from that of hydrogen-1. For example in the normal chemical analysis, nuclei of flourine-19, of phosphorus-31 and carbon-13 are utilized.

As described hereinbefore in detail, since the density and relaxation times of the specific atomic nucleus are measured by utilizing the NMR phenomenon, chemical information of this nucleus can be obtained.

It should be noted that the NMR signals introduced in the present specification involve echo pulses, or echo pulse signals and also free induction decay signals (referred to as "FID signals" hereinafter). The following embodiments will involve only the echo pulse signals.

There is known "a spin echo method" as one of measuring methods for utilizing these echo signals. According to this spin echo method, an "echo" signal of the NMR signal is measured after $2\tau$ time periods by using $90°$-$\tau$-$180°$ -$2\pi$-$180°$-$2\pi$-$180°$ pulse series, "$\tau$" being a predetermined wait time. It is understood that angles of 90° and 180° of the applied pulses are determined by the following equation (2) under the strength of the applied magnetic field and the applied time of the pulse "tp";

$$\theta = \gamma H_1 tp [rad] \tag{2}$$

As is well known, there is a Nuclear Magnetic Resonance-Computerized Tomographic Apparatus (referred to as "NMR-CT apparatus") in which using this echo signal, a distribution of the spin density of a specific atomic nucleus in a certain imaginary slice of the object is processed in the a computer so as to reconstruct a tomographic image of the slice. According to a recent development in this technical field, a phase detection technique is newly introduced in order to utilize frequency information of the detected echo signals. However there are still difficulties that the echo signals are very weak, and random noises caused by the receiver channels and the object are superimposed to the above-described very weak echo signals, resulting in a low signal-to noise (S/N) ratio. Consequently there exists an extreme difficulty in that only pure signals induced by the NMR phenomenon are selectively detected.

It is therefore an object of the present invention to provide an NMR diagnostic apparatus in which an S/N ratio of the NMR signal induced by the nuclear magnetic resonance phenomenon can be improved.

SUMMARY OF THE INVENTION

Those objects and other features of the invention may be accomplished by providing a nuclear magnetic resonance diagnostic apparatus comprising: means for applying a static magnetic field to the object under observation; signal transmitter means for exciting that object to generate a nuclear magnetic resonance (NMR) signal from a planar portion of that object; means for detecting those NMR signals; means for temporarily storing that detected NMR signal and for improving the signal-to-noise (S/N) ratio thereof by undertaking a summation of a plurality of signal components of the detected NMR signal; and means for processing the detected NMR signal, the S/N ratio of which is improved, so as to obtain a tomographic image of that portion of the object.

In one preferred embodiment, the signal transmitter means excites an observed portion of the object identially for a plurality of successive examination periods, the detecting means detects the NMR signals from that portion of the object during successive examination periods, and the S/N ratio improving means operates such that at least one of the cosine signal components or one of the sine signal components which were taken during one of the examination periods is summed with one of the cosine signal components or one of the sine signal components which were taken during one of the examination periods, respectively.

In an alternative preferred embodiment the signal-to-noise ratio improving means operates such that at least two of the cosine components or two of the sine signal components taken during one examination period are summed together with each other, respectively.

BRIEF DESCRIPTION OF THE DRAWINGS

For a better understanding of these and other objects of the present invention, reference is had to the following detailed description of the invention to be read in conjunction with drawings in which.

DETAILED DESCRIPTION OF THE PREFERRED EMBODIMENTS

Before preceeding with the various preferred embodiments, a principle of the NMR diagnostic apparatus and methods in accordance with the present invention will be explained.

The basic idea of the NMR diagnostic apparatus and methods is as follows:

An NMR signal particularly, an echo signal, derived from a probe head coil is processed in a phase detection circuit, especially a quadrature detector.

After temporarily storing the detected NMR signal into adequate memory means, this detected signal is processed in an S/N ratio improving circuit.

In the S/N ratio improvement circuit, for example, a first cosine signal component (referred to as "cos signal") and also a first sine signal component (referred to as "sin signal") of the detected NMR signals which were taken in a first examination period at the given slice of the object and temporarily stored in the memory means, are summed in phase by second ones which were taken in a second examination period at the same slice as in the first examination period and temporarily stored in the memory means.

In accordance with the above-described basic idea, a first description will now be made of four methods for improving the S/N ratio of the NMR signal (the echo signal in this embodiment).

Figure 1A:
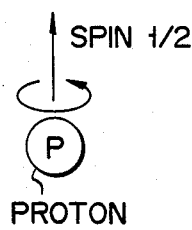
FIGS. 1A, 1B, 2A, 2B, 3A and 3B are illustrative representations for explaining nuclear magnetic moment.
Figure 1B:
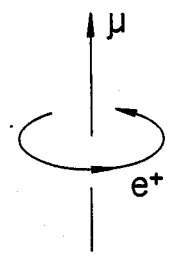
Figure 2A:
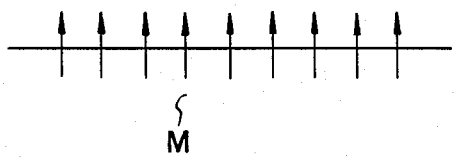
Figure 2B:
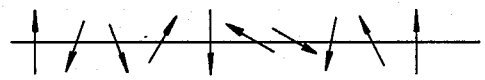
Figure 3A:
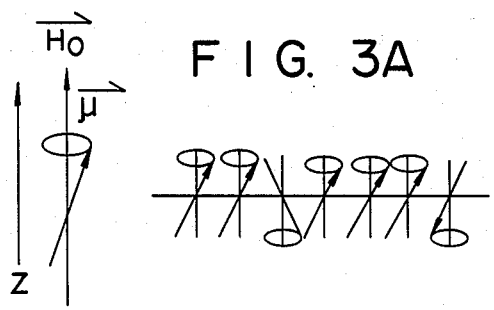
Figure 3B:
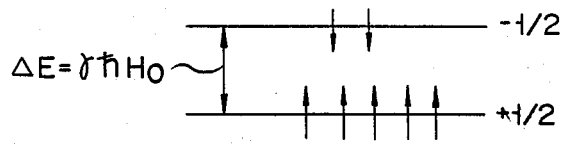
Figure 4:
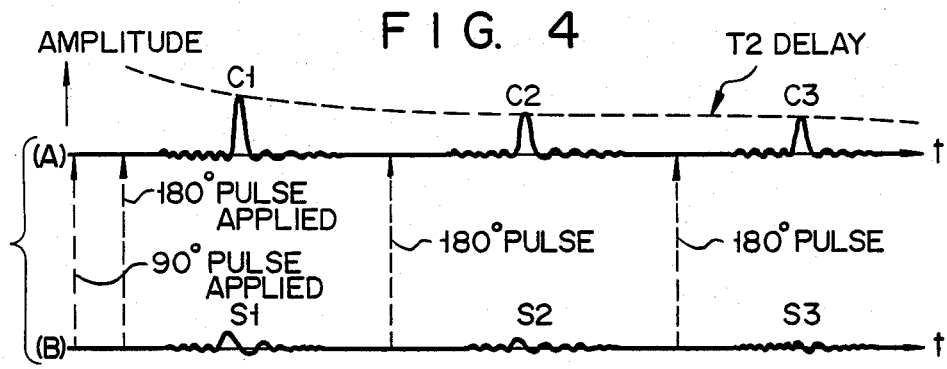
FIGS. 4A and 4B show waveforms of an echo signal casued by the NMR phenomenon.

In the normal echo signal collection by utilizing a quadrature detector (which will be described later), signals shown in FIGS. 4A and 4B are obtained during one examination period. Those signals are derived in such a manner that the collected NMR signals are quadrature-detected based upon two reference signals (which will be described later) which have the same frequency as the resonant frequency and their own phases different from each other. The signal shown in FIG. 4A is a so-called "cos signal component", and also the remaining signal in FIG. 4B is a so-called "sin signal component". An amplitude of the echo signal is represented in the vertical axis, and a time lapse is in the horizontal axis. Those signals can be obtained by, e.g. Carr-Purcell method, Meibroom-Gill method, or CPMG method.

During one examination period of the echo signal collection, a selective exciting pulses series composed of $90°\text{-}\tau\text{-}180°\text{ -}2\tau\text{-}180°\text{-}2\tau\text{-}180°$ pulses are applied to the object. "$\tau$" is given time interval.

1. First Method

Figure 5:
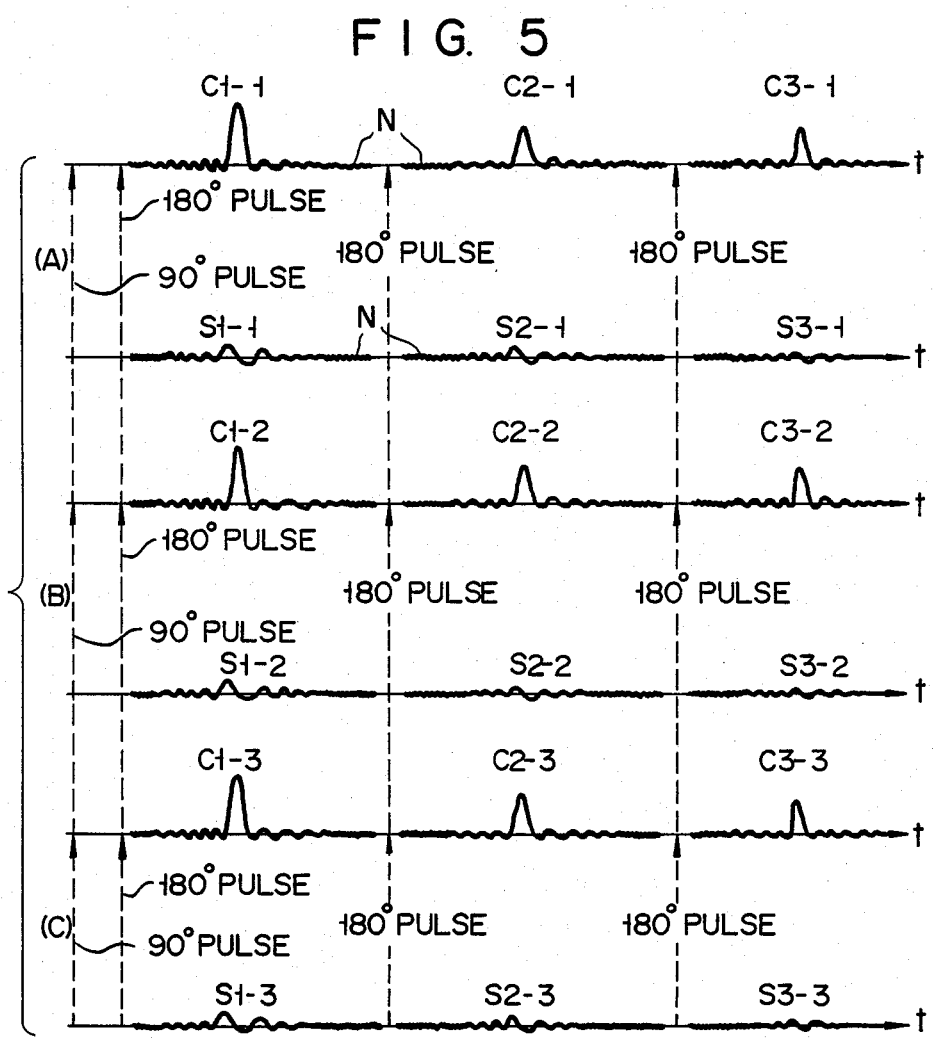
FIGS. 5A, 5B and 5C show waveforms of the echo signals which are quadrature-detected in an NMR diagnostic apparatus according to one preferred embodiment of the invention.

As already described, when the echo pulse signals necessary for diagnostic purposes are acquired, the same selective exciting pulses are applied plural times to the same slice portion of the object (in this embodiment, 3 times). As a result, a plurality of the echo pulse signal series are collected as shown in FIGS. 5A, 5B and 5C. For instance, the echo pulse signal series shown in FIG. 5A is obtained during a first examination period.

It should be noted that since the signal waveforms shown in FIGS. 5A, 5B and 5C indicate the quadrature-detected signal waveforms of the NMR signals, one echo pulse signal series consists of, e.g., the cos signal components C1-1, C2-1 and C3-1, as well as the sin signal components S1-1, S2-1 and S3-1.

In accordance with a first S/N ratio improvement method, the cos signal components of the echo signal series C1-1, C1-2 and C1-3 that were taken during each examination period, are summed together. That is, the echo signal series are acquired time-sequentially by applying the same exciting pulses to the same slice portion, so that three series of the echo pulse signals are subsequently obtained during three examination periods, C1-1, C2-1, C3-1; S1-1, S2-1, S3-1: C1-2, C2-2, C3-2; S1-2, S2-2, S3-2: C1-3, C2-3, C3-3; S1-3, S2-3, S3-3. Then the cos signal components of the echo signal series, e.g., (C1-1, C1-2 and C1-3) are simply summed (i.e., the summing number is three). As shown in FIG. 5A, suppose that random noises "N" are superimposed to all sin signal components S1-1, S2-1, . . ., S3-3 and all cos signal components C1-1, C2-1, . . ., C3-3 during every examination period. So, as a result of the above-described summation, although for example, the summed cos signal components (C1-1, C1-2 and C1-3) become approximately three times larger than one of the cos signal components, the randam noises "N" are not multiplied three times. Consequently it can be readily understood that the S/N ratio of the echo signal components is improved by the summation according to this first method.

Moreover not only the second cos signal components (C1-2, C2-2, C3-2) but also the third cos signal components (C1-3, C2-3, C3-3) are summed respectively in accordance with the first method. That is, for example the summation is carried out for the second cos signal components; C1-2, C2-2, and C3-2.

It is obvious that this summation should be carried out for the sin signal components, e.g., S1-1, S1-2 and S1-3. To obtain a distribution characteristic of the relaxation time "T2" and the computerized tomographic images of the slice portion, both the cos signal components and the sin signal components are processed in the S/N ratio improvement circuit after performing the summation defined by the first method.

2. Second Method

In this method, all cos signal components, or all sin signal components of the echo signal series are summed, e.g., C1-1, C2-1, C3-1 or S1-1, S2-1, S3-1 which are collected during the same examination period. That is, for instant, the cos signal components C1-1, C2-1 and C3-1 taken during one examination period have different amplitudes from each other. Those signal components are merely summed.

Figure 6:
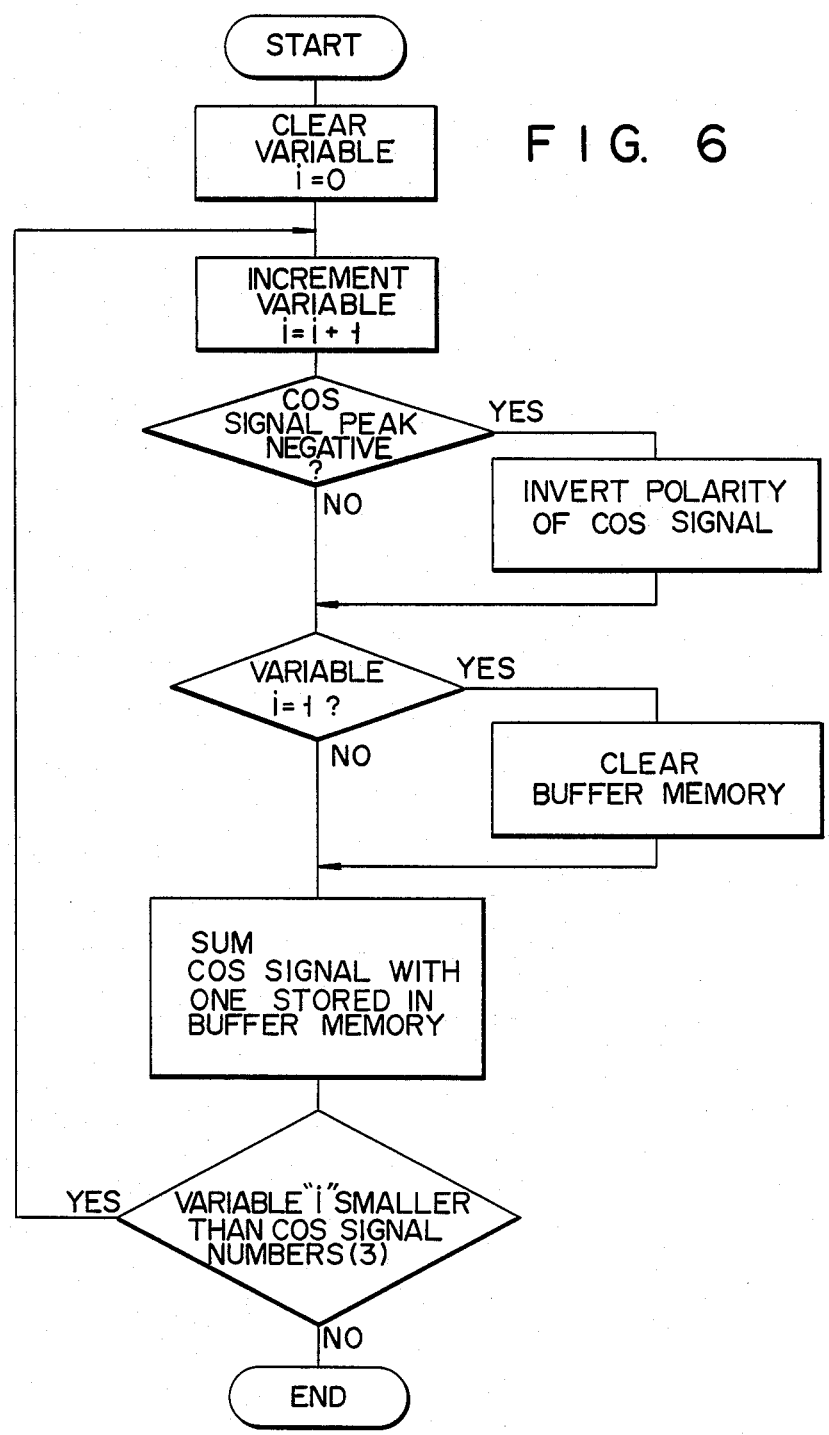
FIG. 6 is a flow chart on the second method of the S/N ratio improvement.

The above-described S/N ratio improving method will be explained with referenct to a flow chart shown in FIG. 6.

As an initial preparation, a variable "i" is cleared so as to recognize the first echo signal, and "1" is set as an initial value, supposing that the cos signal components of the echo signal shown in FIG. 5A are "Cn". Thereafter the following sequential operation is carried out:

Increment the variable "i" by 1.

Secondly judge whether the cos signal peak is negative or not. If it is negative, invert the polarity of the cos signal. There is a case that the polarity of the every two echo signals is changed, depending on the phase of the 180° pulse carrier wave.

Thirdly judge whether the variable is equal to "1" or not (namely, judge whether the present cos signal component is the first one or not). If yes, then clear the buffer memory (not shown) for the cos signal components of the echo signal. If no, sum the present cos signal component by the cos signal component stored in the buffer memory. Then, compare the variable '37 i" with the number of the echo signal component ("3" in the condition shown in FIG. 5A). If the number is greater than the variable "i", the operation is still continued from the increment step with an increment of the variable "i". When the incremented variable "i" becomes greater than the number of the cos signal component, this processing flow is accomplished. Thereafter the results of the processed signal component are subjected to an examination of the spin density or an arithmetic processing of the relaxation time.

Furthermore, this processing flow may be applied to not only the remaining cos signal components C1-2, C1-3 etc., but also the sin signal components S1-2, S1-3 etc. so as improve the S/N ratio thereof.

3. Third Method

Figure 7:
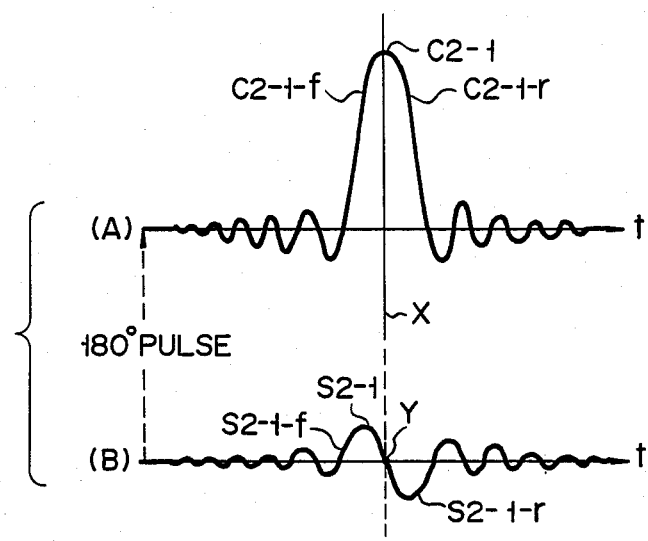
FIGS. 7A and 7B show waveforms of one of the echo signals for explaining the third method of the S/N ratio improvement.

In this method, the echo signal series as shown in FIGS. 5A, 5B and 5C are collected and stored in the adequate memory in advance the same as in the previous methods. For example if each one of the echo signal series is considered, e.g., the cos signal component C2-1 and the sin signal component S2-1 as shown in FIG. 7A and 7B respectively, the former component C2-1 has a line-symmetrical relation with respect to a solid line "X", and the latter component S2-1 has a point-symmetrical relation with respect to a point "Y". According to the third method, waveform portions of the cos signal component C2-1 which are composed by a front waveform portion C2-1-f and a rear waveform portion C2-1-r are summed with maintaining the above-described line-symmetrical relation. In other words, the front portion C2-1-f is added to the rear portion C2-1-r by folding the front portion over the rear one with respect to the symmetrical line X, as it were. Thereafter the summed waveform portion is averaged. As a result, the noise component contained in the cos signal component C2-1 can be relatively reduced and also the S/N ratio can be improved.

The similar summing method is also applied to the sin signal component S2-1. However there is one different point that due to the point-symmetrical relation, the polarity of either waveform portio S2-1-f or S2-1-r should be inverted before the summation.

Figure 8:
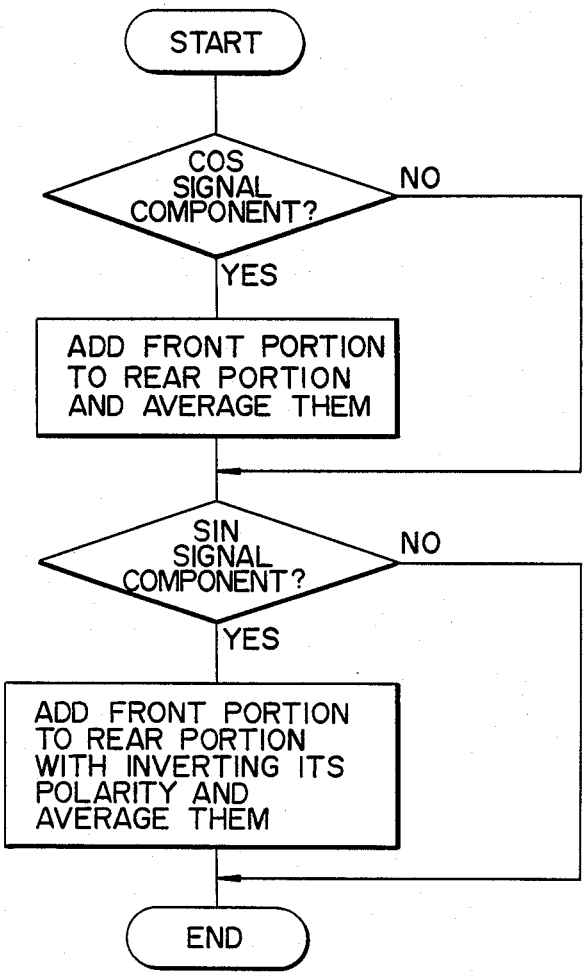
FIG. 8 is a flow chart on the third method of the S/N ratio improvement.

A flow chart shown in FIG. 8 describes the third method:

First, judge whether the input echo signal corresponds to the cos signal component, e.g., C2-1 or not. If yes, sum the front portion C2-1-f by the rear portion C2-1-r and average the results of the summation. If no, judge whether the input echo signal corresponds to the sin signal component, e.g., S2-1 or not.

Secondly if it is the sin signal component S2-1, add the front portion S2-1-f to the rear portion S2-1-r having first inverted the polarity of the rear portion or the front portion, and then take an average of the summation.

The process flow is accomplished.

4. Fourth Method

The fourth method is one to combine more than two methods which were previously described. That is, there are four combinations that the first and second methods, the second and third methods, the third and first methods, and the first, second and third methods.

Figure 9:
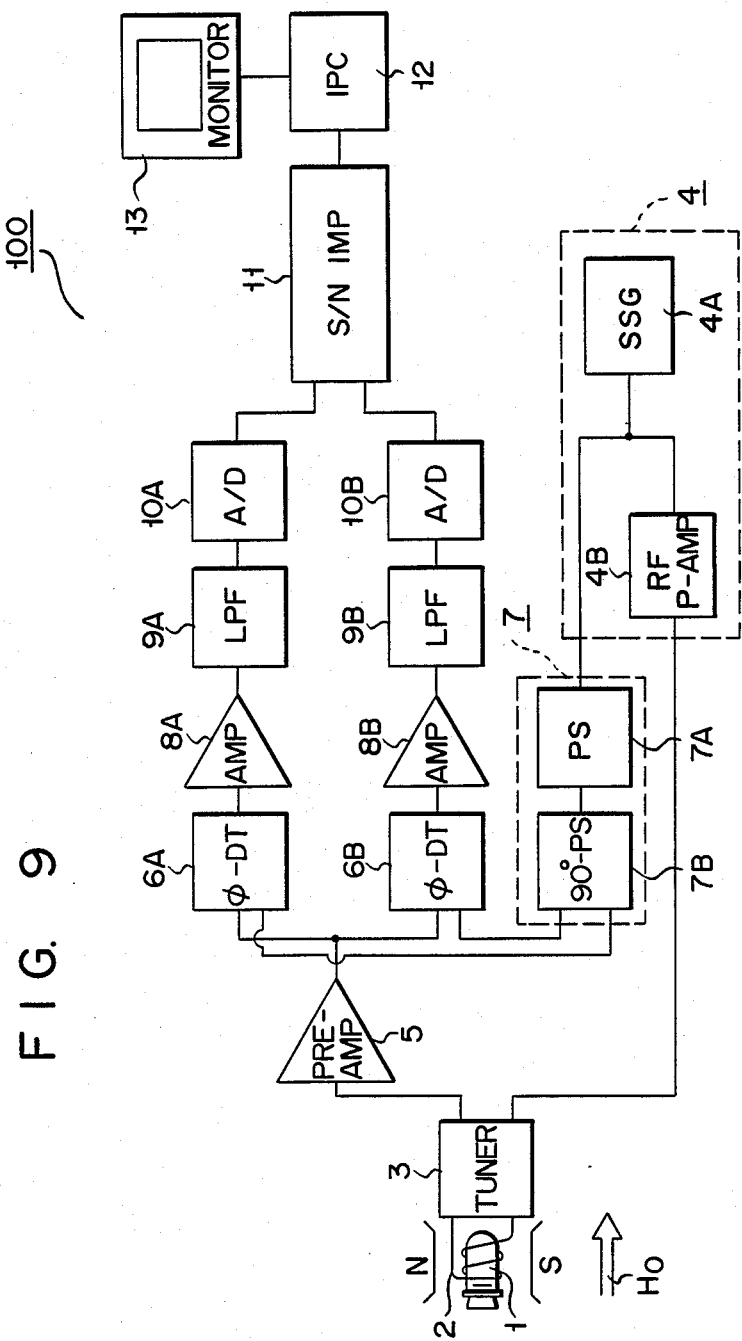
FIG. 9 shows a block diagram of the NMR diagnostic apparatus according to one preferred embodiment in which the quadrature detection is employed.

FIG. 9 shows a circuit diagram of an NMR diagnostic apparatus according to one preferred embodiment in which one of the above-described S/N ratio improving method is employed.

The NMR diagnostic apparatus 100 is comprised of the following components. The object 1 such as a patient is arranged in a static magnetic field $H_O$ that is produced by an electromagnet (not shown), and simultaneously in a transmitter/receiver coil 2 which is positioned in such a manner that a magnetic field produced by the trasmitter/receiver coil 2 intersects with the static magnetic field $H_O$ at a right angle. A tuner 3 is connected to the transmitter/receiver coil 2 and has the following function to select an electromagnetic wave having a specific frequency from the electromagnetic waves generated by a transmitter 4 and to be tuned to a specific nuclei, e.g., hydrogen-1 in the object 1 by applying the selective exciting pulse (corresponding to the aforementioned electromagnetic wave having the specific frequency) to the transmitter/receiver coil 2. The transmitter 4 is constructed by a standard signal generator 4A (referred to as "SSG") and an RF (radio-frequency) power amplifier 4B. The RF signal containing the selective exciting RF pulse signal having e.g., a frequency of 4,258 MHz is generated from the SSG 4A and then amplified in the RF power amplifier 4B to a given power. Precisely speaking, the above-mentioned RF pulse is produced in such a manner that the standard signal generated by SSG 4A is frequency-modulated in a frequency modulator (not shown) by pulse signals from a pulse generator (not shown). Accordingly those frequency modulator and pulse generator constitute an RF pulse generator. On the other hand, this RF signal is applied to a reference signal generator 7 (will be described later) as a reference signal.

Then a description will now be made of a receiving system.

A preamplifier 5 is connected to the tuner 3 so as to amplify the NMR signals (the echo pulse signals in this embodiment) which are received through the transmitter/receiver coil 2, and thereafter to apply the amplified echo pulse signals to two phase detectors 6A and 6B respectively. Those phase detectors 6A, 6B are designed to operate as the quadrature detector. A reference signal generator 7 is comprised of a phase shifter 7A and a 90° phase shifter 7B so as to generate two reference signals whose phases are different from each other at 90° and which have the same frequency as that of the echo signals. Those reference signals are applied to the phase detectors 6A and 6B respectively. Accordingly since the echo signal which has been amplified in the preamplifier 5 is separatedly supplied to those phase detectors 6A and 6B, the echo signal is quadrature-detected therein based upon the two reference signals. Thus two detected signals in an analogue form are independently amplified in amplifiers 8A and 8B, and thereafter filtered in low pass filters 9A and 9B so as to eliminate the RF signal components therefrom. Those filtered signal waveforms are represented in FIGS. 5A, 5B and 5C. The filtered analogue signals are converted by A/D converters 10A and 10B into corresponding digital signals. Those digitalized signals are input in an S/N ratio improvement circuit 11. This circuit 11 has mainly such two functions that the digitalized signals are temporarily stored, and also one of the S/N ratio improving methods as previously described is carried out therein. Subsequently two signals which have been improved with respect to their S/N ratios are supplied to an image processing circuit 12 wherein the spin density and the relaxation time are calculated. Consequently diagnostic information on the object 1 by the nuclear magnetic resonance phenomenon can be obtained which may be displayed on a monitor 13.

The embodiments just described will now be summarized.

That is, the echo signal series are quadrature-detected with two reference signals which have the frequency identical to the resonant frequency of the NMR signal, and whose phases are different from each other at 90 degrees. Then those quadrature-detected signals are converted into respective digital signals, S/N ratios of which may be improved in the following stage. If those improvd signals are utilized in the NMR diagnostic apparatus, it can be obtained extremely high quality CT images of the object.

While the invention has been described in terms of certain preferred embodiments, and examplified with respect thereto, those skilled in the art will readily appreciate that various modifications, changes, omissions may be conceived by those skilled in the art.

First, in the previous embodiments, the quadrature detection circuit (7, 6A and 6B) was employed. As the invention is not limited to this type of the detection circuit, the normal phase detection circuit can be employed. In this case, one signal detection processing path of the detector 6A — the amplifier 8A — low pass filter 9 — A/D converter 10A, or the detector 6B — the amplifier 8B — low pass filter 9B — A/D converter 10B can be omitted.

Secondly, an S/N ratio of the echo pulse signals was improved according to the above-described four methods after performing one of four methods in the S/N improvement circuit 11. It is also possible that the detected NMR signals in an analogue form are directly processed in the S/N ratio improvement circuit 11 in which an analogue memory such as a video tape recorder, or a video disc may be utilized.

In the previous embodiments there are employed the selective exciting pulses such as 90°-τ-180° pulses. It is however, possible to introduce alternatively the normal exciting pulses to excite the slice of the object.

What is claimed is:

1. An apparatus for examining an object by nuclear magnetic resonance comprising:
   means for applying a static magnetic field to said object;
   signal transmitter means for exciting said object to generate a nuclear magnetic resonance (NMR) signal from a planar portion of said object, said NMR signal having a plurality of sine signal components and a plurality of cosine signal components;
   means for quadrature detecting said NMR signal;
   means for temporarily storing said detected NMR signal and for improving the signal-to-noise (S/N) ratio thereof by obtaining a resultant NMR signal comprising at least one of: (i) a summation in phase of a plurality of said sine signal components of said detected NMR signal to result in a summation of sine signal components and (ii) a summation in phase of a plurality of said cosine signal components of said detected NMR signal to result in a summation of said cosine signal components; and
   means for processing said resultant NMR signal, the S/N ratio of which is improved, so as to obtain a tomographic image of said portion of said object.

2. An apparatus of claim 1 further including analog-to-digital converting means for converting said detected NMR signal into digital form.

3. An apparatus for examining an object by nuclear magnetic resonance comprising:
   means for applying a static magnetic field to said object;
   signal transmitter means for exciting said object to generate a nuclear magnetic resonance (NMR) signal from a planar portion of said object;
   means for quardrature detecting said NMR signal and for separating said NMR signal into a series of cosine signal components of said NMR signal and a series of sine signal components thereof;
   analog-to-digital converting means for converting said cosine signal components and said sine signal components into corresponding digital cosine and sine signal components of said NMR signal, respectively;

means for temporarily storing said digital cosine and sine signal components and for improving the signal-to-noise (S/N) ratio of said NMR signal by obtaining a resultant NMR signal comprising a summation in phase of said digital cosine signal components and/or summation in phase of said digital sine signal components; and means for processing said resultant NMR signal, the S/N ratio of which is improved, so as to obtain a tomographic image of said portion of said object.

4. An apparatus as recited in claim 3 wherein:

said signal transmitter means excites said portion of said object identically for a plurality of successive examination periods;

said detecting means detects said NMR signal during said successive examination periods; and said S/N ratio improving means operates such that at least one of said cosine signal components which were taken during one of said examination periods is summed with an in phase corresponding one of said cosine signal components which were taken during a successive one of said examination periods.

5. An apparatus as recited in claim 3 wherein:

said signal transmitter means excites said portion of said object identically for a plurality of successive examination periods;

said detecting means detects said NMR signal during said successive examination periods; and said S/N ratio improving means operates such that at least one of said sine signal components which were taken during one of said examination periods is summed with an in phase corresponding one of said sine signal components which were taken during successive one of said examination periods.

6. An apparatus as recited in claim 3 wherein:

said signal transmitter means excites said portion of said object for a plurality of successive examination periods;

said detecting means detects said NMR signal during said successive examination periods; and said S/N ratio improving means operates such that at least two of said cosine signal components, or at least two of said sine signal components, which were taken during one of said examination periods and in phase with each other, are summed with each other.

7. An apparatus as recited in claim 3 wherein:

said S/N ratio improving means operates such that one waveform portion of one of said cosine signal components is summed with another waveform portion of that cosine signal component, or one waveform portion of one of said sine signal components is summed with another waveform portion of that sine signal component.

8. A method for examining an object by nuclear magnetic resonance imaging comprising the steps of:

applying a magnetic field to said object;

applying exciting pulses to said object to generate a nuclear magnetic resonance (NMR) signal from a planar portion of said object, said NMR signal having a plurality of sine signal components and a plurality of cosine signal components;

detecting said NMR signal in a quadrature manner;

summing in phase a plurality of said sine signal components with one another and/or summing in phase a plurality of said cosine signal components with one another to improve the signal-to-noise (S/N) ratio of said detected NMR signal; and processing said improved S/N ratio NMR signal to obtain a tomographic image of said portion of said object.

9. A method of claim 8 wherein:

said step of applying exciting pulses to said object includes applying a series of identical exciting pulses to said object for a plurality of successive examination periods to generate said NMR signal from said portion of said object during each of said examination periods; and said step of detecting includes detecting said NMR signal during said successive examination periods.

10. A method of claim 9 wherein:

said step of summing includes adding together corresponding in phase cosine signal components detected during successive examination periods.

11. A method of claim 9 or 10 wherein:

said step of summing includes adding together corresponding in phase sine signals components detected during successive examination periods.

12. A method of claim 8 wherein said step of detecting includes detecting said NMR signal for a plurality of successive examination periods.

13. A method of claim 12 wherein:

said step of summing includes adding together in phase cosine signal components detected during the same examination period.

14. A method of claim 12 or 13 wherein said step of summing includes adding together in phase sine signal components detected during the same examination period.

15. A method of claim 8 wherein:

said step of summing comprises adding together one waveform portion of one of said cosine signal components with another waveform portion of said cosine signal component.

16. A method of claim 8 or 15 wherein:

said step of summing comprises adding together one waveform portion of one of said sine signal components with another waveform portion of said sine signal component.

* * * * *